(12) United States Patent
Baker et al.

(10) Patent No.: US 7,104,148 B2
(45) Date of Patent: Sep. 12, 2006

(54) METHOD AND APPARATUS FOR EVALUATING THE FLOWABILITY OF CORE FORMING MATERIALS

(75) Inventors: Stephen G. Baker, Spencer, IN (US); Joshua M. Werling, Fishers, IN (US)

(73) Assignee: International Engine Intellectual Property Company, LLC, Warrenville, IL (US)

( * ) Notice: Subject to any disclaimer, the term of this patent is extended or adjusted under 35 U.S.C. 154(b) by 197 days.

(21) Appl. No.: 10/954,602

(22) Filed: Sep. 30, 2004

(65) Prior Publication Data
US 2006/0070427 A1    Apr. 6, 2006

(51) Int. Cl.
*G01N 1/00* (2006.01)
(52) U.S. Cl. ........................................... 73/866
(58) Field of Classification Search ............... 73/863.71
See application file for complete search history.

(56) References Cited

U.S. PATENT DOCUMENTS

| | | | | |
|---|---|---|---|---|
| 2,531,083 A | * | 11/1950 | Smith | .................. 73/19.01 |
| 3,083,577 A | * | 4/1963 | Moore et al. | ............ 73/863.71 |
| 5,165,291 A | * | 11/1992 | Galetto et al. | ................ 73/866 |
| 6,112,131 A | * | 8/2000 | Ghorashi et al. | ........... 700/142 |
| 6,158,293 A | * | 12/2000 | Poole | .......................... 73/866 |
| 2005/0199077 A1 | * | 9/2005 | Prybella et al. | .......... 73/863.86 |

* cited by examiner

*Primary Examiner*—Robert Raevis
(74) *Attorney, Agent, or Firm*—Susan L. Lukasik; Dennis K. Sullivan; Jeffrey P. Calfa

(57) ABSTRACT

A method and apparatus for evaluating the flowability of a core-forming material in which an airborne core-forming material is blown downwardly into a first, downwardly extending, long and confining passageway for a predetermined time, and the airborne core-forming material is allowed to escape the first long, confining passageway by diverting it into a short, transverse passageway, and further diverting it into a second, upwardly extending confining passageway, and the flowability of the core-forming material is evaluated from the quantity of core-forming material that has entered the second, upwardly extending confining passageway.

17 Claims, 1 Drawing Sheet

METHOD AND APPARATUS FOR EVALUATING THE FLOWABILITY OF CORE FORMING MATERIALS

FIELD OF THE INVENTION

This invention relates to the evaluation of materials for use in the formation of cores, and more particularly relates to methods and apparatus for the evaluation of flowability of core-forming materials, such as core sands and prepared core sand-resin mixtures.

BACKGROUND OF THE INVENTION

The testing of core-forming materials is an important part of foundry operations. Core breakage is a common phenomena in foundry practice, and the ability to compare the performance of various core sands and core sand-resin mixtures and to predict, in advance, core sand and core sand mixtures that will provide unacceptable performance is obviously beneficial. There are several test methods that are used to evaluate the ability of core sand and core sand mixtures to produce reliable cores. Several of the test methods used in the past to evaluate core-forming materials include the core tensile or dog bone method, the transverse disk, and the transverse load method in which cores 1"×1"× 8" (2.54 cm×2.54 cm×20.32 cm) are formed for testing. Such testing methods include testing of core strength, in which cores are made and broken in a transverse mode, core deflection, which is a measure of how much a core bends before breaking, which relates to core breakage attributed to core brittleness, core sand flowability, which evaluates the ease with which a prepared core-forming materials flow when blown into a core box, and core shrinkage, which relates to the ability of core sand mixtures to provide reliable casting dimensions.

The flowability of core sand mixtures is an important characteristic in the production of reliable cores. Core sand flowability is affected by a variety of variables, such as sand temperature, sand shape and size, resin percentage, and core additive types and amounts The ever-thinning core sections needed for modern castings make it especially important to determine the ease or difficulty with which a prepared core-forming material moves. How easily a prepared core sand mixture flows is important to good core formation, core density and strength. In the manufacturing of cores, prepared core sands must frequently flow downwardly, laterally, and then upwardly, to fill some small core area. An example of such requirements includes a water core jacket for an engine block head. The ability to determine in advance how well a core sand, core-sand-resin mixture, or other core-forming material will reliably produce a given core is important in choosing the right resin system or the right sand, or resin-sand mixture for use in production.

In the past, core sand flowability has been measured with a core box having a spiral core-forming passageway, and the flowability of core-forming materials in this system was measured by the distance core sand or core sand mixtures or other core-forming materials traveled down the spiral. While the results obtained with this prior core sand flowability test method were usable, a flowability testing method and apparatus that more closely represents what happens in actual production operations is desired.

SUMMARY

An apparatus for testing the flowability of mixtures for forming cores for castings comprises a metal test fixture forming a pair of substantially parallel core-forming passages joined adjacent their one ends by a transverse passageway. Included are vent openings at their one ends, an inlet for core-forming materials at the other end of one of the substantially parallel core-forming passages, and means for admitting a flow of airborne core-forming material in the inlet opening at the other end of the one of the substantially parallel core-forming passageways.

DETAILED DESCRIPTION

Figure 1:
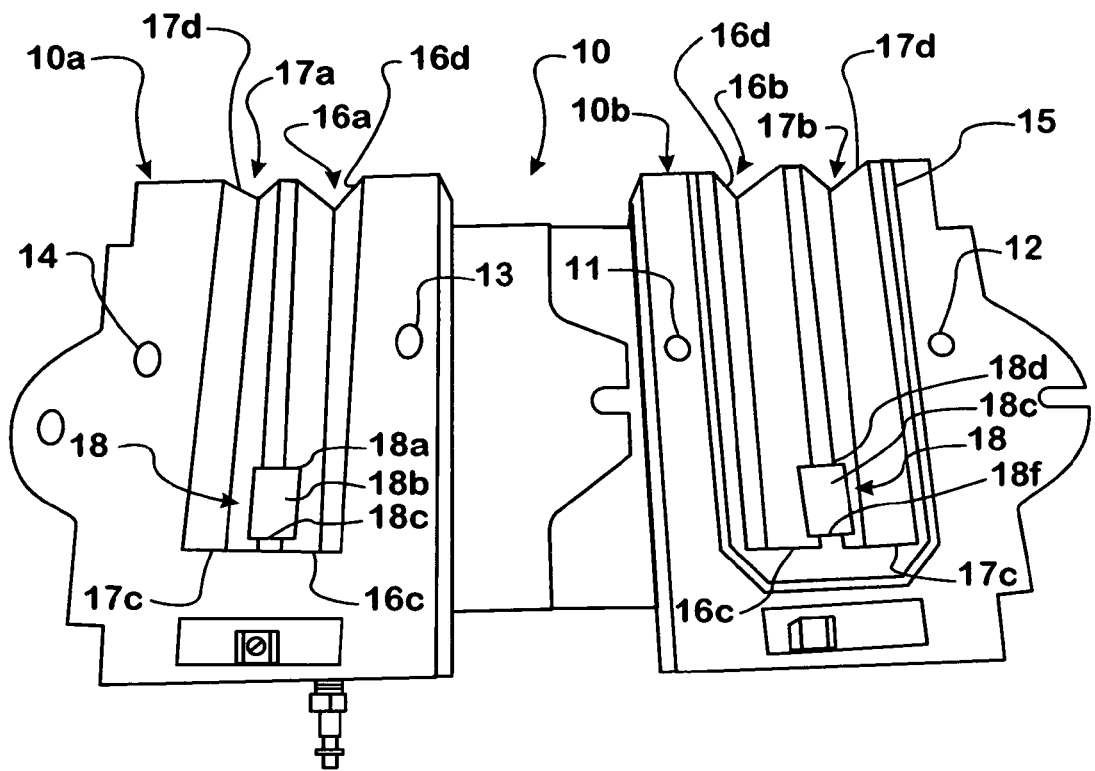
FIG. 1 is an illustration of a test fixture opened to show its internal configuration in accordance with the invention.

A method and apparatus for evaluating and quantifying the flowability of a core-forming material are provided. In the method, the flowability of a core-forming material is evaluated by blowing an airborne core-forming material downwardly into a first, downwardly extending, long and confining passageway for a predetermined time, and allowing the airborne core-forming material to escape the first long, confining passageway by diverting it into a short, transverse passageway, and further diverting it into a second, upwardly extending confining passageway, and evaluating the flowability of the core-forming material from the quantity of core-forming material that has entered the second, upwardly extending confining passageway.

A test fixture forms a pair of substantially parallel core-forming passageways several inches long that are adjoined adjacent their one ends by a transverse passageway. The test fixture includes vent openings at the one ends of the pair of substantially parallel passageways, and has an inlet opening at the other end of a first one of the core-forming passageways for the admission of core-forming material. Such a test fixture may be easily formed by the addition of a transverse passageway to the core-forming fixture used in the transverse load method of testing. In the method, core-forming material is blown into the inlet opening of the test fixture until the core-forming material fills the one core-forming passageway that includes the inlet opening. The core-forming material in the test fixture is then cured, and the test fixture is opened to remove the cured core-forming material. The flowability of the core-forming material is evaluated from the quantity of core-forming material that has entered the second one of the pair of substantially parallel core-forming passageways.

In one embodiment, the pair of substantially parallel core-forming passageways have a cross-section area of about an inch, and the transverse passageway has an area of about 1.15 square inches, and a length of about 0.50 inches, and still more preferably, the pair of substantially parallel core-forming passageways each have a square cross-section that is about 1 inch by 1 inch, and the transverse passageway has a rectangular cross-section of about 1 5/16 inches by about 7/8 inch. In a particularly preferred metal text fixture, each of the substantially parallel core-forming passageways is about 8 inches in length.

A flowability number is determined by weighing the total quantity of cured, core-forming material that has been received in the test fixture, weighing the quantity of the core-forming material that has entered only the second one of the pair of passageways, and dividing the weight of the quantity of the core-forming material that has entered only the second one of the pair passageways by the weight of the total quantity of core-forming material that has been received in the test fixture.

Different core-forming materials may be used and the flowability numbers of the different core-forming materials may be recorded for comparison and future use by comparing the flowability numbers with the actual performance of the different core-forming materials in production. The method and apparatus may provide data permitting the selection of core-forming materials for use in production.

A test fixture 10 for use in determining the flowability of core-forming materials is shown in FIG. 1. The test fixture 10 is shown with its two halves 10a, 10b open and separated to illustrate the interior of the test fixture. A top portion that cooperates with the two portions 10a, 10b to close the top end of the fixture 10 and form an inlet to one of the core-forming passageways of the test fixture 10 is not shown. In use, the test fixture half 10b, shown on the right of FIG. 1, is joined with the test fixture half 10a to form two substantially parallel core-forming passageways, for example the test fixture half 10b may be placed on top of the test fixture half 10a. The test fixture half 10b is located with respect to the test fixture half 10a by the engagement of the holes 11, 12 formed in the test fixture half 10b on the locating pins 13, 14, respectively, that protrude from the open face of the test fixture half 10a. The test fixture half 10b carries a seal member 15 to seal the interface between the test fixture halves 10a, 10b when they are mated.

As apparent from FIG. 1, the test fixture 10, when assembled, forms a pair of substantially parallel core-forming passages 16 and 17, one half of the core-forming passages 16b, 17b, respectively, are formed in the test fixture half 10b, and the other half of the pair of substantially parallel core-forming passages 16a, 17a are formed by the test fixture half 10a. As further illustrated by FIG. 1, a transverse passageway 18 is formed adjacent the one ends 16c, 17c of the passageways 16, 17 by the removal of material from the portions of each of the test fixture halves 10a, 10b between the passageway halves 16a, 17a and 16b, 17b that are formed in the die halves 10a, 10b, respectively. When the test fixture halves 10a, 10b are mated, the transverse passageway is formed by surfaces 18a, 18b and 18c of test fixture half 10a and surfaces 18d, 18e and 18f of test fixture half 10b. The transverse passageway may be formed by milling the portion of each test fixture half (10a, 10b) that lies between the pair of substantially parallel core-forming passages 16, 17. The test fixture 10 is provided with vent openings for each of the pair of substantially parallel core-forming passageways 16, 17 at their one ends 16c, 17c. The vent openings, which are not shown in the figures, may be formed in either test fixture half 10a or test fixture half 10b, or at the interface between the two test fixtures halves 10a, 10b. Preferably, the test fixture halves 10a, 10b, when assembled, form a pair of substantially parallel core-forming passageways 16, 17 having a length of several inches and a cross-section of about one square inch, and the transverse passageway 18 adjacent their one ends 16c, 17c preferably has a cross-sectional area of about 1.15 square inches. It is particularly preferable that each of the pair of the substantially parallel passageways 16, 17 have a square cross-section about 1 inch by about 1 inch, and that the transverse passageway has a rectangular cross-section about 1 5/16 inches by about 7/8 inch and a length of about 1/2 inch. The other ends 16d, 17d of the pair of substantially parallel passageways 16, 17 are closed, when the test fixture is assembled, by a block (not shown) that forms an inlet for core-forming material, permitting airborne core-forming material to be directed into one of the core-forming passageways 16 or 17.

As further indicated below, the test fixture 10 for evaluating the flowability of core-forming materials forms a pair of substantially parallel core-forming passageways 16, 17 several inches long and joined adjacent their one ends 16c, 17c by a transverse passageway 18, and with vent openings at their one ends 16c, 17c, and with an inlet opening at the other end of one of the core-forming passageways 16 or 17 for the admission of airborne core-forming material. In a method for evaluating the flowability of a core-forming material, the core-forming material is blown into the inlet opening until the core-forming passageway 16 or 17 receiving the airborne core-forming material is filled. The core-forming material in the test fixture is then cured, as it would be in production operations, and the test fixture is opened so the cured core-forming material may be removed. The flowability of the cured core-forming material is evaluated by determining the quantity of core-forming material that has entered the second one of the pair of substantially parallel core-forming passageways. That is, if the inlet for the airborne core-forming materials is in communication with the passageway 16, the flowability of the core-forming material is determined by the quantity of core-forming material that has entered passageway 17. The core-forming material is preferably blown into the test fixture with the same apparatus that is used in producing cores for production use.

Thus, in the method described above, airborne core-forming material is blown downwardly into a first downwardly extending long, confining passageway for a predetermined time, and allowed to escape the first long, confining passageway by its diversion into a short, transverse passageway and its further diversion into a second, upwardly extending, confining passageway, thereby allowing the flowability of the core-forming material to be evaluated from the quantity of the core-forming material that has entered the second upwardly extending confining passageway.

Figure 2:
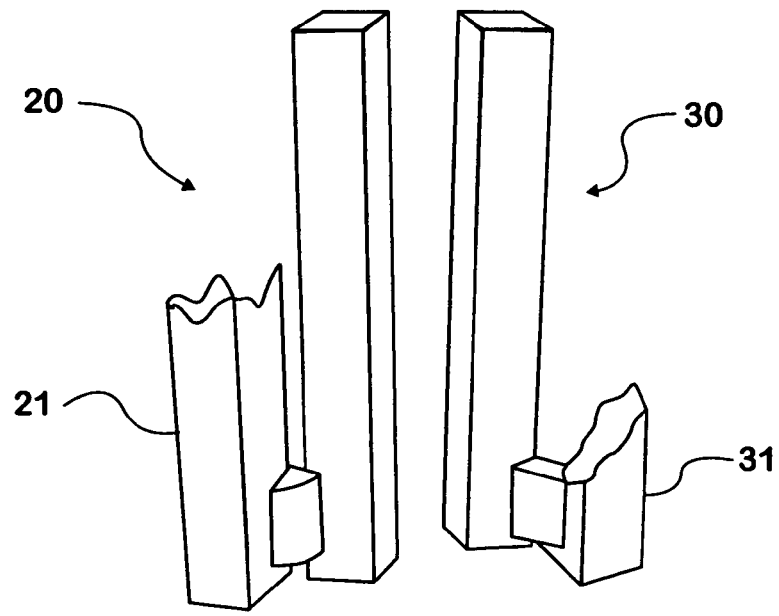
FIG. 2 is a perspective view of two cores that have been formed in the test fixture of FIG. 1 with different core-forming materials in accordance with the invention.

FIG. 2 illustrates two different cured, core-forming materials that have been removed from the test fixture illustrated in FIG. 1. As indicated by a comparison of the samples 20 and 30, the core-forming material used in the formation of the sample 20 was more flowable than the core-forming material used in the sample 30. This is because the quantity of core-forming material in the cured core-portion 21 is greater than the quantity of cured, core-forming material in the sample portion 31.

The method permits the flowability of different core-forming materials to be quantified. For example, by weighing the total quantity of cured, core-forming material in the sample 20 and in the sample 30, then cutting from the cured samples 20 and 30, the sample portions 21 and 31, being careful to maintain the uniformity of the cross-section of the sample portions 21 and 31 (that is, in the samples illustrated in FIG. 2, wherein each of the substantially parallel core-forming portions have a square cross-section of one inch by one inch, the portions 21 and 31 are removed from the samples 20 and 30 so that the cut portions of the sample portions 21 and 31 have a square cross-section of one inch by one inch). The sample portions 21 and 31 so formed are weighed and by dividing the weight of the sample portions 21 and 31 by the original total weight of the samples 20 and 30, and multiplying the result by 100, a flowability number (percentage result) may be generated that represents the flowability of each of the different core-forming materials that were used in the formation of samples 20 and 30.

Other examples demonstrate how flowability numbers may be used to evaluate the differences in different core-forming materials. Five tests were run using a test fixture and method as described above, with each of the pair of substantially parallel core-forming passageways 16, 17 having a square cross-section one inch by one inch on the side, and a length of eight inches, with a transverse passageway adjacent their one ends having a rectangular cross-section, 1$\frac{5}{16}$ inches long and $\frac{7}{8}$ inch wide, forming a transverse passageway length of about $\frac{1}{2}$ inch. By processing the cured core-forming material removed from the test fixture following each test, as set forth above, flowability numbers for 5 different core-forming materials were obtained. In the first example a core-forming material having 0.5% resin and the balance silica sand, when evaluated, had a flowability number of 20.89. In the second test, a core-forming material comprising 0.75% resin and the balance lake sand gave a flowability number of 20. In the third test, a core-forming material having 1.1% resin and the balance lake sand gave a flowability number of 19.06. In the fourth test, a core-forming material having 1.65% of resin plus 3.5% of anti-veining agent and the balance lake sand gave a flowability number of 17.98, and in the fifth test, a core-forming material having 1.65% resin and 6% anti-veining agent and the balance lake sand gave a flowability number of 17.17. The resin used in the test was a phenolic urethane cold box resin. All percentages are by weight.

The invention provides numerous advantages. The development of flowability numbers for different core-forming materials that may be correlated with the performance of the different core-forming materials in production so that collection and retention of such flowability data on different core-forming materials may assist in the selection and rejection of different core-forming materials for use in the manufacture of cores of different configurations is advantageous.

The present invention may be embodied in other specific forms without departing from its spirit or essential characteristics: The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed is:

1. A method of evaluating the flowability of a core-forming material comprising the steps of:
   providing a test fixture forming a pair of substantially parallel core-forming passages several inches long and joined adjacent their one ends by a transverse passageway, with vent openings at their one ends and with an inlet opening at the other end of a first one of the core-forming passageways for admission of core-forming material;
   blowing the core-forming material into the inlet opening until the first one core-forming passageway is filled;
   curing the core-forming material in the test fixture;
   opening the test fixture and removing the cured core-forming material; and
   evaluating the flowability of the core-forming material from the quantity of core-forming material that has entered the second one of the pair of substantially parallel core-forming passageways.

2. The method of claim 1, wherein the pair of substantially parallel core-forming passageways have a cross-sectional area of about 1 square inch, and the transverse passageway has a cross-sectional area of about 1.15 square inches and a length of about 0.50 inches.

3. The method of claim 2, wherein the pair of substantially parallel core-forming passageways each have a square cross-section that is about 1 inch by 1 inch and wherein the transverse passageway has a rectangular cross-section about 1$\frac{5}{16}$ inch by about $\frac{7}{8}$ inch.

4. The method of claim 2, wherein each of the substantially parallel core-forming passageways is about 8 inches long.

5. The method of claim 1, wherein a flowability number is determined by weighing the total quantity of cured core-forming material that has been removed from the test fixture, cutting the cured core-forming material that has been removed from the test fixture to produce a sample including only cured core-forming material that has entered the second one of the pair of substantially parallel core-forming passageways, weighing the sample of the cured, core-forming material that has entered the second one of the pair of substantially parallel passageways, and dividing the weight of the sample of cured, core-forming materials that has entered the second one of the pair of substantially parallel passageways by the weight of the total quantity of cured, core-forming material that has been removed from the test fixture.

6. The method of claim 5, wherein different core-forming materials are used and the flowability numbers of the different core-forming materials are recorded for comparison and future use and for comparison with the actual performance of the different core-forming materials in production.

7. An apparatus for testing the flowability of mixtures for forming cores for castings comprising a metal test fixture forming a pair of substantially parallel core-forming passages joined adjacent their one ends by a transverse passageway, and including vent openings at their one ends, an inlet for core-forming materials at the other end of one of the substantially parallel core-forming passages, and means for admitting a flow of airborne core-forming material in the inlet opening at the other end of the one of the substantially parallel core-forming passageways.

8. The apparatus of claim 7, wherein the core-forming passageways have a square cross-section one inch by one inch and a length of eight inches.

9. The apparatus of claim 8, wherein the transverse passageway has a length of $\frac{1}{2}$ inch and a cross-sectional area of 1.15 square inches.

10. The apparatus of claim 7, wherein the means for admitting a flow of airborne core-forming material into the metal test fixture comprises the same means used in producing cores in production.

11. The apparatus of claim 7, wherein each of the pair of substantially parallel core-forming passageways has a cross-sectional area of about 1 square inch and the transverse passageway has a cross-sectional area of about 1.15 square inches.

12. A method of evaluating the flowability of a core-forming material comprising the steps of:
   blowing an airborne core-forming material downwardly into a first, downwardly extending, long, confining passageway for a predetermined time;
   allowing the airborne core-forming material to escape the first long, confining passageway by diverting it into a short, transverse passageway, and further diverting it into a second, upwardly extending, confining passageway; and evaluating the flowability of the core-forming material from the quantity of core-forming material that has entered the second, upwardly extending, confining passageway.

13. The method of claim 12, wherein the first, downwardly extending, long, confining passageway and second, upwardly extending, confining passageway have a cross-sectional area of about one square inch, and the short transverse passage has a cross-sectional area of about 1.15 square inches and a length of about 0.50 inches.

14. The method of claim 13, wherein the first and second long confining passageways each have a square cross-section that is about one inch by about one inch and the short transverse passageway has a rectangular cross-section about 1 5/16 inches by about 7/8 inch.

15. The method of claim 12, wherein the long confining passageways are each about eight inches long.

16. The method of claim 12, wherein a flowability number is determined by weighing the total quantity of core-forming material that has been received within the first and second long confining passageways and the short transverse passageway, weighing the quantity of the core-forming material that has entered only the second long confining passageway, and dividing the weight of the quantity of cured core-forming material that has entered only the second long confining passageway by the weight of the total quantity of cured core-forming material that has entered the first and second long confining passageways and the short transverse passageway.

17. The method of claim 16, wherein different core-forming materials are used and the flowability numbers of the different core-forming materials are recorded for comparison and future use and for comparison with the actual performance of the different core-forming materials in production.

* * * * *